United States Patent [19]
Marrujo et al.

[11] Patent Number: 5,215,885
[45] Date of Patent: Jun. 1, 1993

[54] STABLE TWO-PART CHROMOGEN SUBSTRATE

[75] Inventors: David J. Marrujo, Woodenville, Wash.; Rose M. Cernosek, Placentia, Calif.; Patrick F. Coleman, Edmonds, Wash.; Charles C. Walbourn, Encinitas, Calif.

[73] Assignee: Beckman Instruments, Inc., Fullerton, Calif.

[21] Appl. No.: 601,847

[22] Filed: Oct. 23, 1990

[51] Int. Cl.$^5$ ............................................. G01N 33/545
[52] U.S. Cl. .................................... 435/794; 435/7.9; 435/7.93; 435/25; 435/28; 435/188; 435/975
[58] Field of Search ................. 435/28, 25, 7.9, 7.93, 435/7.94, 810, 188, 975

[56] References Cited

U.S. PATENT DOCUMENTS

| | | | |
|---|---|---|---|
| 4,234,680 | 11/1980 | Hevey et al. | 435/7.94 |
| 4,239,743 | 12/1980 | Sedlacek et al. | 424/12 |
| 4,444,879 | 4/1984 | Foster et al. | 435/7.95 |
| 4,503,143 | 3/1985 | Gerber et al. | 435/7.36 |
| 4,525,452 | 6/1985 | Jones et al. | 435/29 |
| 4,596,770 | 6/1986 | Parham et al. | 435/28 |
| 4,824,784 | 4/1989 | Cantarow | 435/7.94 |
| 4,891,314 | 1/1990 | Pauly et al. | 435/28 |

FOREIGN PATENT DOCUMENTS

3641489 6/1987 Fed. Rep. of Germany ........ 435/28

*Primary Examiner*—Mary E. Ceperley
*Attorney, Agent, or Firm*—William H. May; Arnold Grant

[57] ABSTRACT

A two part peroxide/chromogen reagent for use in peroxidase labeled binding assays which is stable for at least about 24 hours is disclosed. The reagent is provided as two components, the first component preferably incorporating a peroxide dissolved in a first solvent, and the second component preferably having a chromogenic substance dissolved in a second solvent where the two components can be mixed within about 48 hours of colorimetric detection of an enzyme immunoassay.

22 Claims, 3 Drawing Sheets

STABLE TWO-PART CHROMOGEN SUBSTRATE

FIELD OF THE INVENTION

The present invention is related to enzyme colorimetric immunoassays, and more particularly to a stable two-part reagent for use with such assays.

BACKGROUND OF THE INVENTION

In recent years, enzyme immunoassay methods have received widespread acceptance in both research and commercial settings for use in the detection and measurement of antibodies or antigens of interest ("ligands") in test samples. Enzyme immunoassay methods involve the ultimate attachment of an enzyme label to a test sample ligand. The attachment may be either direct or indirect through enzyme-labeled immunocomplexes which bind specifically to the test sample antigen or antibody. The enzyme, in turn, catalyzes a reaction with a substrate to produce detectable signal.

The same general methods can be employed for the determination of ligands of interest other than antigens and antibodies. For example, where the ligand of interest is a piece of genetic material, such as a target nucleotide sequence, enzyme-labeled nucleic acid probes can be used to assay the target nucleotide of interest in a test sample. See, for example, U.S. Pat. No. 4,581,333, which is incorporated herein by reference.

Typical enzyme-labeled specific binding assays include both competitive and non-competitive, i.e. sandwich, type enzyme-labeled specific binding assays for ligands of interest. In a competitive enzyme-labeled specific binding assay method, a predetermined quantity of enzyme-labeled ligand competes with unlabeled test sample ligand for the available binding sites on a limited amount of insolubilized specific binding partner. The amount of insolubilized, or bound, enzyme-labeled ligand can be measured, with the amount of test sample ligand being determined by the relative proportion of specific binding partner—enzyme labelled ligand to specific binding partner—non-labelled ligand. The amount of ligand in the sample is indirectly proportional to the amount of enzyme-labelled ligand bound to the insolubilized specific binding partner. The specific binding partner can itself be bound to a second insolubilized binding partner.

In a non-competitive, or sandwich type specific binding assay, a first specific binding partner to the ligand of interest is insolubilized on a supporting membrane, particle, or similar material. A second specific binding partner to the ligand, preferably having a binding site(s) on the ligand different from that of the first specific binding partner, is labeled with an enzyme. The first and second specific binding partners will "sandwich" the ligand of interest, with the first insolubilized specific binding partner providing a means for separating the bound enzyme-labeled ligand from the free labeled ligand in solution. Alternatively, the first specific binding partner may be provided with a means for subsequent insolubilization after the desired sandwich complex is formed. The amount of labeled sandwich formed bears a direct relationship to the amount of ligand of interest present in the test sample.

The enzyme label in an enzyme-labeled specific binding assay provides a means of quantifying the amount of ligand present in a test sample once the desired labeled complex is formed. This is ordinarily accomplished by adding an excess of enzyme substrate to the solution containing the labeled complex. The substrate typically contains a chromogenic material which yields a colored product that can be conveniently detected both visually and instrumentally, such as with a spectrophotometer. The amount of ligand of interest in a test sample is directly or indirectly proportional to the "amount" of color produced by enzymatic action on the chromogenic material.

Where an excess of substrate is added, the rate of color change of the chromogen is independent of the substrate concentration, and the enzyme concentration becomes the rate-limiting factor in the overall color reaction. I.e., the rate of color change is a function of the enzyme concentration which is, in turn, a function of the amount of ligand of interest present in the test sample. This is important where measurement is accomplished by an instrument, because it allows for rapid quantification based on rate measurement, rather than the lengthy wait required to achieve a result in an end point method.

Typical enzymes that have been used in enzyme-labeled specific binding assays include peroxidase, glucose oxidase, $\beta$-D-galactosidase, and alkaline phosphatase. The term "peroxidase" as used herein refers to any enzyme exhibiting oxidase or peroxidic activity and includes, for example, horseradish peroxidase, catalase, tyrosine oxidase and the like, Both $\beta$-D-galactosidase and alkaline phosphatase are found in normal human urine; they are not ordinarily preferred for use in connection with enzyme-labeled specific binding assay techniques. Horseradish peroxidase, on the other hand, is not ordinarily found in human test samples. It is also plentiful, inexpensive, and stable, and has a high conversion rate of various chromogens in the presence of a peroxide to yield colored products.

The typical substrate for the enzyme horseradish peroxidase is a solution of a peroxide, such as hydrogen peroxide or urea peroxide, combined with a chromogenic material. Horseradish peroxidase first catalyzes the decomposition of the enzyme substrate peroxide. The degradation product then reacts with the chromogenic material to produce a chromophore which can be measured visually or spectrophotometrically. One of the most sensitive chromogenic materials available for detection of peroxidase activity is ortho-phenylenediamine (OPD), which is initially soluble and colorless in aqueous solution, but produces a yellowish-orange chromophore upon oxidation in the presence of a peroxide. Other chromogenic materials which are useful in the detection of peroxidase activity include: o-tolidine; 2,2'-azinobis(3-ethylbenzothiazoline-6-sulfonic acid) diammonium salt (ABTS); m-phenylenediamine; dianisidine; aniline; phenol red; pyrogallol; 4-aminoantipyrine; and bromopyrogallol red.

Previous OPD reagents are provided as one-part reagents with a substrate buffer being combined with the peroxide and chromogen. See generally, U.S. Pat. No. 4,234,680; U.S. Pat. No. 4,467,031; U.S. Pat. No. 4,444,879; U.S. Pat. No. 4,504,587; U.S. Pat. No. 4,520,113, as representative of the use of peroxide substrates and OPD chromophore, each of which is incorporated herein by reference. Commercially available OPD in a convenient tablet form may be obtained from a number of sources such as, for example, Beckman Instruments, Inc. (Product Number 688035—each tablet contains: 10 mg ortho-phenylenediamine plus mannitol, sodium carbonate, citric acid and polyethylene glycol).

One of the primary disadvantages of, for example, a peroxidase—OPD system is that the substrate can be oxidized by air to yield the same colored products. E.g., when a solution of OPD is dissolved in a peroxide and substrate buffer and left to stand alone, without the presence of a peroxidase enzyme, the OPD chromogen, in as little as one hour, rapidly oxidizes to a yellow-orange color. The air oxidation of the substrate can result in high blank values (defined as elevated absorbance values in the absence of enzyme activity), artificially high results, and other related problems. This, in turn, has an adverse effect on the reproducibility and precision of enzyme-labeled specific binding assays using a peroxidase—OPD system. To accommodate this problem, conventional chromogenic reagents are preferably prepared in fresh batches immediately prior to use. See, for example, U.S. Pat. No. 4,239,743, Col. 7, lines 12-18, and U.S. Pat. No. 4,503,143, Col. 3, lines 44-48, which are incorporated herein by reference.

This is a distinct disadvantage with enzyme immunoassays which themselves require multiple fluid transfers and manipulations, including addition of reactants, mixing, separation of solid and liquid phases, removal of unreacted components and undesired reaction products, washings, etc. These steps usually must be repeated over and over in order to achieve the desired end result; as such, these manipulations require a lot of time, which is at a premium in a clinical laboratory. Having to mix a fresh batch of chromogenic reagents for each assay thus exacerbates an already difficult problem and all but excludes the use of automated assay instruments that are designed to run such assays over extended time periods.

It would be advantageous to have a conventional substrate solution for peroxidase that exhibits improved stability over previous solutions, such that a fresh batch of reagent need not be prepared for each assay.

SUMMARY OF THE INVENTION

The present invention satisfies the above listed need by providing a stable two-part peroxide/chromogen substrate, or reagent, for use in peroxidase-labeled binding assays. The present invention finds particular usefulness in automated assay instruments. The reagent is provided as two separate components, with the first component having the peroxide dissolved in a solvent, and the second component having the chromogen also preferably dissolved in a solvent. In a most preferred embodiment, the solvents are buffers and the buffers are the same or substantially the same, the chromogen is OPD, the peroxide is urea peroxide, and the peroxidase is horseradish peroxidase. The two-part substrate exhibits surprising and extended stability over previous one-part substrates (where substrate and chromagen are combined as a single solution mixture).

DETAILED DESCRIPTION OF A PREFERRED EMBODIMENT OF THE INVENTION

The present invention utilizes a stable two-part chromogenic reagent for color development in peroxidase-labeled specific binding assays. The reagent is separated into two components, rather than the single component of previous reagents. A solvent is provided for both components, and preferably, the solvent is a buffer. A first component includes a peroxide which is dissolved in the buffer to form an aqueous solution. A second component can incorporate a chromogenic material in dissolved form within the buffer, although the chromogenic material may be maintained in solid form (or other similar form) and dissolved in the second component (including the buffer), prior to mixture with the contents of the first component.

Chromogenic materials which are useful include o-tolidine; 2,2'-azinobis(3-ethylbenzothiazoline-6-sulfanic acid) diammonium salt (ABTS); m-phenylenediamine; dianisidine; o-phenylenediamine (OPD); aniline; phenol red; pyrogallol; 4-aminoantipyrine; and bromopyrogallol red. Most preferably, the chromogenic material is OPD.

The buffer can be citric acid-potassium phosphate-dibasic in an approximate 1:1.85 molar ratio (hereinafter "phosphate citrate"), potassium citrate, or sodium citrate, preferably either a phosphate citrate or sodium citrate buffer. The pH of the buffer should be in the range of from about 4.0 to about 5.5; preferably the pH is about 4.8. The substrate can be hydrogen peroxide, methyl peroxide, ethyl peroxide, or urea peroxide. Preferably, the substrate is hydrogen peroxide; most preferably, urea peroxide is used as the substrate. A germicide can be added to the buffer, thimerosal being an example of a suitable germicide.

The two-part substrate of the present invention may be used in any type of peroxidase-labeled specific binding assay. For example, the two-part substrate of the present invention may be employed in both conventional competitive and sandwich type specific binding assay methods.

A peroxidase-labeled competitive binding assay performed in accordance with the teachings of the present invention comprises: (1) the ligand of interest, (2) insolubilized specific binding partner for the ligand of interest, (3) peroxidase-labeled ligand of interest, and, (4) the two-part substrate of the present invention. The ligand from a test sample is incubated with a known amount of peroxidase-labeled ligand and insolubilized specific binding partner for the ligand. After incubation for a designated period of time, the ligand that is bound to the insolubilized specific binding partner for the ligand is separated from the ligand in solution and the enzymatic activity of the solid or liquid phase is determined following addition of the two-part reagent to either of the two phases. Each part of the two-part reagent is preferably added separately. Colorimetric measurements are based on conversion of the chromogen, e.g. OPD, from the second component to its corresponding yellow-orange colored product in the presence of the peroxide from the first component.

Similarly, a peroxidase-labeled sandwich type specific binding assay performed in accordance with the teachings of the present invention comprises: (1) the ligand of interest, (2) insolubilized specific binding partner for the ligand of interest, (3) peroxidase-labeled specific binding partner for the ligand of interest, and, (4) the two-part substrate of the present invention. The ligand of interest, from a test sample, is allowed to react with the insolubilized component. Unreacted ligand is then removed, e.g. by washing, and peroxidase-labeled specific binding partner for the ligand is added. Following reaction, unreacted peroxidase-labeled specific binding partner is removed and the enzyme activity of the solid or liquid phase is determined in the same manner as set forth for a competitive assay.

The two-part substrate exhibits surprising stability over previous one-part substrates. The surprising and unexpected results as disclosed herein are obtained by the separation of the chromogenic material in one component, from the peroxide included in a separate component. This separation allows for, at a minimum, at least 24 hours for stability of the separated components. Accordingly, the present two-part substrate is particularly applicable and useful in automated assay systems that perform numerous assays over extended time periods.

EXAMPLES

The following Examples are presented for illustration purposes only and are not intended to limit the scope of the invention, this disclosure, or the claims that follow.

EXAMPLE 1

Preparation Of Two-Part Substrate

A two-part substrate using OPD as the chromogenic material was prepared as follows:

A phosphate citrate buffer ("reagent buffer") was prepared by dissolving 6.73 g citric acid, 11.32 g potassium phosphate-dibasic and 0.1 g thimerosal in distilled water, and making the resulting solution up to 1.0 L in volume. The phosphate citrate buffer thus prepared had a molarity of 0.035M citric acid, 0.065M potassium phosphate-dibasic (an approximate 1:1.85 molar ratio), and 0.01% thimerosal. The pH was adjusted to 4.8 by dropwise addition of 6N HCL.

The two-part substrate was thereafter prepared using the phosphate citrate buffer:

| First Component ("A") | Second Component ("B") |
|---|---|
| 3.30 g/L urea peroxide in reagent buffer | 1 OPD tablet (10 mg/tablet) Beckman Instruments, Inc.) in 4 mL reagent buffer |

The separated components A and B can be stored for approximately two-days (amber glass, 4° C.), nearly 24 times the period of time exhibited by conventional one-part OPD substrates. Theoretically, however, by not dissolving the OPD tablet in B, i.e., by having the second component include only 4 mL of reagent buffer, the three components can be stored under the above conditions in excess of two days.

As defined, "Working Substrate/Buffer" or "WS/B" is analogous to a one-part substrate, and is the combination of components A and B. The WS/B can be made by combining effective ratio amounts of components A and B just prior to use. For the preferred embodiment that makes use of the automated instrument referenced in Example II, this ratio volume is about 1 part A to five parts B (1:5). Thus, to achieve 30 mL of WS/B, 5 mL of A is combined with 25 ml of B. The WS/B is stable for approximately 1-2 hours after preparation.

EXAMPLE II

One- And Two-Part Substrate Blank Comparison

In order to compare one-part versus two-part substrate solution stability over time, absorbance readings of the one- and two-part substrate reagents were taken over several different time periods following dissolution of the OPD tablet in the respective buffers. Time periods were tested at zero time (T+0); plus four hours (T+4); plus 9 hours (T+9); plus 13 hours (T+13); and, plus 25 hours (T+25).

U.S. Pat. No. 4,871,683, which is assigned to the assignee of the present invention and which is incorporated herein by reference, discloses an "Apparatus And Method Using A New Reaction Capsule". The system and method set forth therein is an example of an automated instrument for a clinical assay (such as an immunoassay) in which the teachings and disclosure of the present invention may be utilized.

For substrate blank comparisons, five capsules were utilized for each of the one- and two-part substrate configurations per time period. Prior to the comparative runs, A and B of Example I were each brought to room temperature. For the one-part substrate, one OPD tablet (Beckman Instruments, Inc., Carlsbad, Calif.) was dissolved in 5 mL of buffer A containing 3.30 g/L urea peroxide. One- and two-part substrate solutions were then refrigerated for about 20 minutes.

For test runs, the one-part substrate was analyzed over time as prepared, whereas for the two-part substrate, mixing of the aforementioned 1:5 ratio amounts of A with B was automatically accomplished by the instrument. At the designated test times, the one- and two-part substrates were added to reaction wells and gently aggitated for approximately one-minute, followed by three separate washings with 400 uL, 450 uL and 500 uL of 0.85% saline solution. At the conclusion of these washings, followed by an additional five minute period, absorbance was measured at 450 nm. Thereafter, average absorbance readings for the five reaction vessels was calculated.

For practical purposes, it is desirable that the absorbance of the substrate blanks remains below about 0.1 absorbance units. Accordingly, "stability" for purposes of these experiments was based upon the ability of the reagent blank to remain below 0.1 absorbance units.

Figure 1:
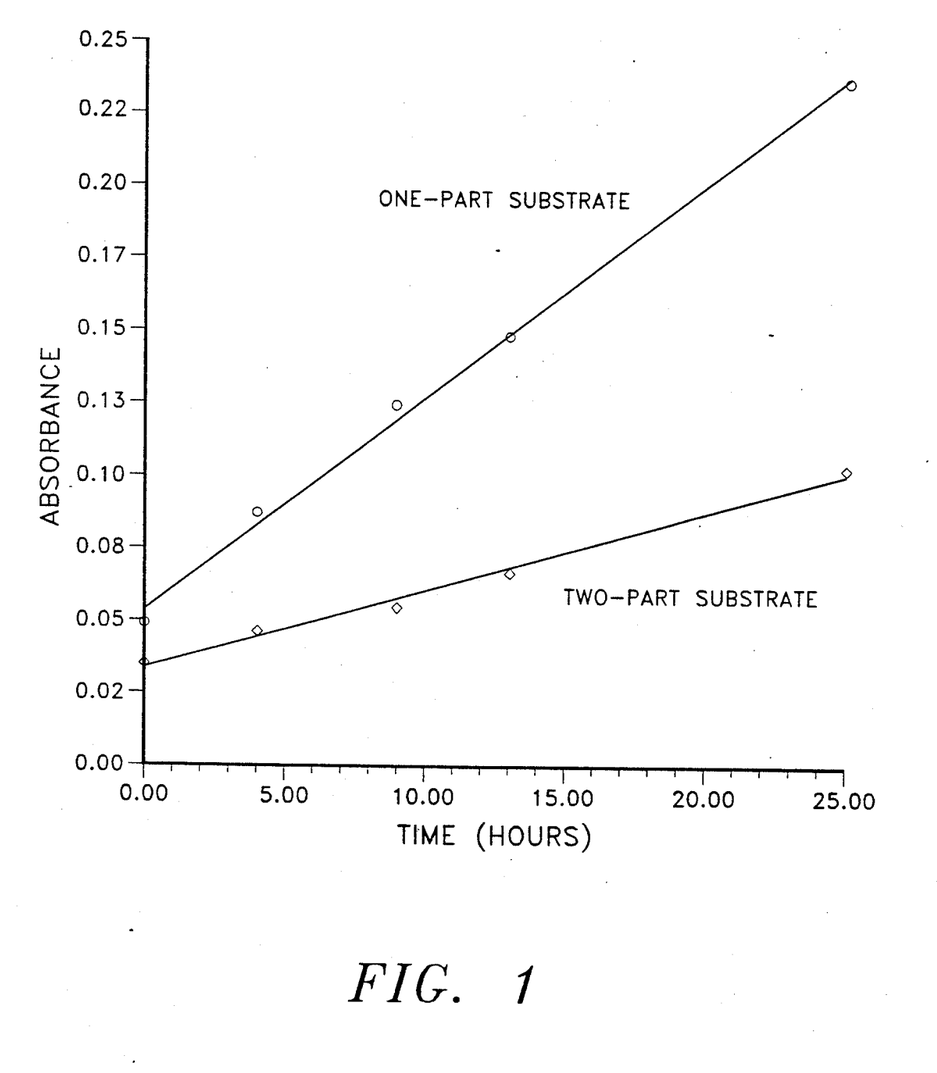
FIG. 1 is a graphic representation of the results of a one- and two-part substrate stability study.

The results of the one- and two-part substrate reagents blanks are set forth in FIG. 1. As depicted therein, the preliminary comparative results indicate that the two-part substrate did not fail the stability criteria (i.e. did not reach 0.1 absorbance units) until approximately 24 hours after Component B was added to Component A, whereas the one-part substrate failed the stability criteria after approximately 6 hours. This data also indicates that the absorbance turnover ("a.t.") for the one-part substrate is greater than 2.5 times the a.t. for the two-part substrate, i.e. one-part substrate a.t. is approximately 0.0072 absorbance units/hour, while the two-part substrate a.t. was approximately 0.0026 absorbance units/hour.

EXAMPLE III

Thyroxin ($T_4$) Enzyme Immunoassay Protocol: One- And Two-Part Feasibility Assays Two-part substrate stability was investigated in terms of assay performance over a time period of 216 utilizing the same two-part substrate addition A and B as set forth in Example I. A thyroxin (T4) EIA protocol was utilized for testing parameters. Each assay consisted of the following:

A) Substrate blanks (located at the front and back of the assay);
B) $B_o$ (defined as maximum binding with zero standard), and
   NSB (defined as non-specific binding in the absence of antibody);
C) T4 serum standards with target values of: 2, 4, 8, 14 and 24 ug/dL; and
D) Control Sera Additionally, a one-part substrate control was run in duplicate and consisted of:

A) Substrate blank;
B) $B_o$ and NSB; and
C) Standards with target values of: 2, 8 and 24 ug/dL.

The one-part substrate was made fresh immediately prior to use and was maintained at room temperature. For the two-part substrate, each component thereof was kept refrigerated between the time intervals. Assays were run for each of the following time intervals after tablet dissolution: zero time (T+0); plus 4 (T+4); plus 8 (T+8); plus 12 (T+12); plus 16 (T+16); plus 24 (T+24); plus 30 (T+30); plus 48 (T+48); plus 72 (T+72); plus 96 (T+96); plus 120 (T+120); plus 168 (T+168); plus 216 (T+216).

Specific reagents utilized were as follows: T4 antibody—Immunosearch—Toms River, N.J., lot #2492 (diluted 1/10,000 in tris-(hydroxymethyl)aminomethane-NaCl-Bovine Serum Albumin-Gelatin (hereinafter "TRIS-NBG") buffer); T4 horseradish peroxidase ("HRP") conjugate—Beckman Instruments, Inc., Fullerton, Calif. (diluted 1/2,000 in TRIS NGB-0.2% 8-anilino-1-napthalene-sulfonic-acid ("ANS") buffer); solid phase Goat-Anti-Rabbit-gamma globulin ("GARGG")—Beckman Instruments, Inc. Fullerton, Calif. (1/35 dilution in TRIS-NBG buffer); T4 Serum Standards, with tentative values assigned of: 0; 2.59; 4.89; 8.95; 14.41 and 24.0 ug/dL—Beckman Instruments, Inc., Fullerton, Calif.; Gilford Control Sera, lot #016B01 (Clinical Assay RIA range: 5.6–8.0 mg/dL), and lot #017B01 (Clinical Assay RIA range; 13.0–19.8 mg/dL); Omega Control Sera—Cooper Biomedical, Malvern, Pa., lot #4814K002 (Clinical Assay RIA range: 4.8–5.6 mg/dL), lot #4824K002 (Clinical Assay RIA range: 8.8–10.2 mg/dL), and lot H 4824K001 (Clinical Assay RIA range: 12.2–16.0 mg/dL); and T4 serum pool—Beckman Instruments, Inc., Fullerton, Calif., low (RIA value assignment—4.96 ug/dL), medium (RIA value assignment—8.65 ug/dL), and high (RIA value assignment—19.88 ug/dL). TRIS-NBG buffer, as previously defined, consisted of 0.05M TRIS, 0.2M NaCl, 0.1% BSA, 0.1% gelatin and 0.02% thimerosal.

Typical one-part substrate addition consisted of substrate buffer with 0.55 g/L urea peroxide and a chromogen, OPD, in tablet form, 10 mg/tablet. One OPD tablet was added to 5 mL of the urea peroxide buffer, and 300 ul of the one-part substrate was added per assay test. The two-part substrate consisted of 50 uL of A and 250 uL of B for each assay test. Most preferably, the OPD tablet is dissolved at room temperature. These concentrations, volumes and temperatures were utilized because they tend to minimize substrate line gassing effects on the instrument.

For the feasibility assays, the aforementioned system and methodology was utilized for testing. All reagents were first brought to room temperature; a new set of antibody and conjugate reagents were utilized for each time period tested. For each reaction well, 100 uL of GARGG was added thereto except to the substrate blank. Thereafter, the following schematic protocol was followed whereby the following reagents were automatically added to each 100 uL GARGG reaction well by the aforementioned instrument:

1) 10 uL Sample
   +
2) 100 uL T4—Ab
   +
3) 100 uL T4 HRP Conjugate
   ↓
4) Incubate 15 min. at 40° C.
   ↓
5) Wash 3 Times
   a) 400uL 0.85% NACL;
   b) 450uL 0.85% NACL; and
   c) 500uL 0.85% NACL
   ↓
6) 300u: Substrate
   a) one part substrate: 300uL
   b) two part substrate: 50uL Formula A +
                          250uL Formula B.
   ↓
7) Incubate 5 min. at 40° C.
   ↓
8) Obtain Absorbance values at 450 nm.

Samples consisted of the aforementioned NSB; T4 Serum Standards; Omega Control Sera; Gilford Control Sera; and Serum Pools. For the one-part substrate, Samples were T4 serum standards; Omega Controls Sera; and Gilford Control Sera.

The one-part substrate served as a control, and, therefore, substrate-chromogen solution was prepared fresh prior to each experimental time point; this prevented drift in the results over time.

RESULTS

Table I summarizes percent $B/B_o$ over time for the results of the one-part substrate controls, with "percent $B/B_o$" being defined as binding of T4 in the presence of known Standard (B), divided by binding of T4 in the absence of Standard ($B_o$) multiplied by 100.

TABLE I

| | Percent $B/B_o$ - One-Part Substrate | | | | | | |
|---|---|---|---|---|---|---|---|
| SAMPLE | 0 HRS | 4 HRS | 8 HRS | 12 HRS | 16 HRS | 24 HRS | 32 HRS |
| NSB | 0.9 | 0.95 | 0.75 | 0.59 | 0.65 | 0.68 | 0.67 |
| $B_o$ ("0" STD) | 100 | 100 | 100 | 100 | 100 | 100 | 100 |
| 2.59 ug/dL | 63.97 | 62.98 | 62.79 | 61.18 | 61.11 | 59.75 | 60.48 |

TABLE I-continued

| Percent B/$B_o$ - One-Part Substrate | | | | | | |
|---|---|---|---|---|---|---|
| 8.95 ug/dL | 34.78 | 33.86 | 33.36 | 32.18 | 32.57 | 32.41 | 31.14 |
| 24.0 ug/dL | — | 15.21 | 14.90 | 14.59 | 14.48 | 15.06 | 14.23 |

| SAMPLE | 48 HRS | 72 HRS | 96 HRS | 120 HRS | 168 HRS | 216 HRS |
|---|---|---|---|---|---|---|
| NSB | 0.77 | 0.62 | 0.98 | 0 | 0.86 | 2.32 |
| $B_o$ ("0" STD) | 100 | 100 | 100 | 100 | 100 | 100 |
| 2.59 ug/dL | 60.83 | 62.90 | 62.22 | 60.02 | 60.58 | 63.09 |
| 8.95 ug/dL | 31.36 | 32.05 | 31.95 | 32.92 | 31.89 | 34.53 |
| 24.0 ug/dL | 14.38 | 14.14 | 13.84 | 14.38 | 13.53 | 15.08 |

Table II summarizes the mean absorbance over time for the results of the controls obtained with one-part substrate prepared fresh at each time period:

TABLE II

| Mean Absorbance - One-Part Substrate | | | | | | | |
|---|---|---|---|---|---|---|---|
| SAMPLE | 0 HRS | 4 HRS | 8 HRS | 12 HRS | 16 HRS | 24 HRS | 32 HRS |
| SUB BLANK | 0.030 | 0.042 | 0.034 | 0.034 | 0.035 | 0.039 | 0.029 |
| NSB | 0.050 | 0.064 | 0.051 | 0.048 | 0.050 | 0.054 | 0.044 |
| $B_o$ ("0" STD) | 2.243 | 2.280 | 2.249 | 2.413 | 2.349 | 2.328 | 2.208 |
| 2.59 ug/dL | 1.453 | 1.459 | 1.431 | 1.495 | 1.455 | 1.413 | 1.353 |
| 8.95 ug/dL | 0.813 | 0.814 | 0.784 | 0.809 | 0.799 | 0.791 | 0.718 |
| 24.0 ug/dL | — | 0.401 | 0.378 | 0.393 | 0.383 | 0.397 | 0.352 |

| SAMPLE | 48 HRS | 72 HRS | 96 HRS | 120 HRS | 168 HRS | 216 HRS |
|---|---|---|---|---|---|---|
| SUB BLANK | 0.028 | 0.026 | 0.032 | 0.028 | 0.330 | 0.030 |
| NSB | 0.046 | 0.040 | 0.053 | — | 0.052 | 0.082 |
| $B_o$ ("0" STD) | 2.163 | 2.200 | 2.202 | 2.164 | 2.210 | 2.244 |
| 2.59 ug/dL | 1.334 | 1.399 | 1.390 | 1.306 | 1.359 | 1.446 |
| 8.95 ug/dL | 0.710 | 0.732 | 0.740 | 0.723 | 0.740 | 0.8285 |
| 24.0 ug/dL | 0.350 | 0.345 | 0.351 | 0.327 | 0.344 | 0.4080 |

Table II summarizes the curve parameters over time for the results of the one-part substrate controls:

TABLE III

| Curve Parameters - One-Part Substrate | | | | | | | |
|---|---|---|---|---|---|---|---|
| CURVE PARAMETERS | 0 HRS | 4 HRS | 8 HRS | 12 HRS | 16 HRS | 24 HRS | 32 HRS |
| SLOPE | 0.9640 | 1.0093 | 1.0167 | 0.9965 | 0.9981 | 0.9517 | 0.9976 |
| $ED_{50}$, ug/dL | 4.74 | 4.50 | 4.44 | 4.16 | 4.19 | 4.02 | 4.00 |

| CURVE PARAMETERS | 48 HRS | 72 HRS | 96 HRS | 120 HRS | 168 HRS | 216 HRS |
|---|---|---|---|---|---|---|
| SLOPE | 0.9963 | 1.0464 | 1.0435 | 0.9817 | 1.0220 | 1.0154 |
| $ED_{50}$, ug/dL | 4.06 | 4.33 | 4.26 | 4.11 | 4.09 | 4.58 |

The data presented in Tables I to III indicates absorbance and percent B/$B_o$ for each one-part substrate assay to be consistent with one another. As NSB percent B/$B_o$ in all control assays is less than 1%, non-specific binding is low with the freshly made one-part substrate. An $ED_{50}$ range of from approximately 4.7 to 4.0 over the 216 hour test period is reasonable. The results thus indicate that the one-part substrate control assays are valid. Because the one-part assays were run in conjunction with the two-part substrate assays, the validity ascribed to the one-part substrate assay validates each two-part substrate assay.

With respect to the $T_4$ EIA two-part substrate assays, gross absorbance values from 0 hours to 216 hours are summarized in Table IV:

TABLE IV

| $T_4$ EIA Two-Part Assay Substrate Assay | | | | | | |
|---|---|---|---|---|---|---|
| SAMPLE | 0 HRS | 4 HRS | 8 HRS | 12 HRS | 16 HRS | 24 HRS |
| FRONT SUB BLK | 0.026 | 0.0490* | 0.0310 | 0.0390 | 0.0470 | 0.0930* |
| NSB | 0.0377* | 0.0677 | 0.0457 | 0.0510 | 0.0620 | 0.0967 |
| STANDARDS | | | | | | |
| $B_o$ ("0" STD) | 2.2300 | 2.442 | 2.3423 | 2.3530 | 2.4327 | 2.4357 |
| 2.59 ug/dL | 1.4403 | 1.5023 | 1.4587 | 1.4953 | 1.4813 | 1.5003 |
| 4.89 ug/dL | 1.0970 | 1.1470 | 1.1060 | 1.1367 | 1.1280 | 1.1393 |
| 8.95 ug/dL | 0.7810 | 0.8237 | 0.8033 | 0.8190 | 0.8313 | 0.8437 |
| 14.41 ug/dL | 0.5667 | 0.5810 | 0.5683 | 0.6010 | 0.5810 | 0.6087 |
| 24.0 ug/dL | 0.3903 | 0.3987 | 0.3973 | 0.4040 | 0.4047 | 0.4163 |

| SAMPLE | 32 HRS | 48 HRS | 72 HRS | 96 HRS | 120 HRS | 168 HRS | 216 HRS |
|---|---|---|---|---|---|---|---|
| FRONT SUB BLK | 0.068* | 0.091 | 0.133 | 0.182 | 0.223 | 0.320 | 0.452 |
| NSB | 0.076 | 0.0917 | 0.1297 | 0.1743 | 0.2167 | 0.308 | 0.435 |
| STANDARDS | | | | | | | |
| $B_o$ ("0" STD) | 2.3303 | 2.343 | 2.4250 | 2.4267 | 2.4333 | 2.534 | 2.596 |
| 2.59 ug/dL | 1.4183 | 1.4377 | 1.4947 | 1.5373 | 1.556 | 1.627 | 1.819 |

TABLE IV-continued

T₄ EIA Two-Part Assay Substrate Assay

| | | | | | | | |
|---|---|---|---|---|---|---|---|
| 4.89 ug/dL | 1.0653 | 1.0890 | 1.1277 | 1.1780 | 1.192 | 1.256 | 1.483 |
| 8.95 ug/dL | 0.7980 | 0.809 | 0.8547 | 0.9100 | 0.920 | 0.980 | 1.192 |
| 14.41 ug/dL | 0.5687 | 0.5873 | 0.6187 | 0.6707 | 0.684 | 0.771 | 0.958 |
| 24.0 ug/dL | 0.3973 | 0.4153 | 0.4520 | 0.4933 | 0.524 | 0.604 | 0.786 |

| | 0 HRS | 4 HRS | 8 HRS | 12 HRS | 16 HRS | 24 HRS |
|---|---|---|---|---|---|---|
| CONTROL SERA | | | | | | |
| OMEGA I | 1.0150 | 1.041 | 1.0560 | 1.0883 | 1.0800 | 1.0507 |
| OMEGA II | 0.6767 | 0.7023 | 0.6830 | 0.7077 | 0.7177 | 0.6987 |
| OMEGA III* | 0.5253 | 0.5430 | 0.5513 | 0.5643 | 0.5640 | 0.5727 |
| GILFORD A | 1.6667 | 1.7083 | 1.7047 | 1.7743 | 1.7640 | 1.7480 |
| GILFORD B | 0.8917 | 0.9347 | 0.8990 | 0.9537 | 0.9567 | 0.9390 |
| GILFORD C | 0.5250 | 0.5370 | 0.4903 | 0.5583 | 0.5690 | 0.5680 |
| SERUM POOLS | | | | | | |
| Low | 1.0683 | 1.1133 | 1.0903 | 1.1723 | 1.146 | 1.1443 |
| Medium | 0.7800 | 0.8117 | 0.7993 | 0.8390 | 0.8183 | 0.8370 |
| High | 0.5750 | 0.5730 | 0.5550 | 0.5997 | 0.6033 | 0.6133 |
| BACK SUB BLK | — | 0.0410 | 0.0370 | 0.0430 | 0.0530 | 0.0670 |

| | 32 HRS | 48 HRS | 72 HRS | 96 HRS | 120 HRS | 168 HRS | 216 HRS |
|---|---|---|---|---|---|---|---|
| CONTROL SERA | | | | | | | |
| OMEGA I | 1.0707 | 1.0270 | 1.0257 | 1.0597 | 1.0930 | 1.1600 | 1.4570 |
| OMEGA II | 0.7043 | 0.7217 | 0.7613 | 0.7880 | 0.8243 | 0.9087 | 1.0890 |
| OMEGA III | 0.5693 | 0.5757 | 0.6053 | 0.6487 | 0.6960 | 0.7623 | 0.9350 |
| GILFORD A | 1.0163 | 1.1067 | 1.1590 | 1.1790 | 1.2030 | 1.2820 | 1.4570 |
| GILFORD B | 0.8020 | 0.8177 | 0.8790 | 0.8987 | 0.9600 | 1.0370 | 1.1830 |
| GILFORD C | 0.5990 | 0.5860 | 0.6380 | 0.6867 | 0.7090 | 0.7850 | 0.9260 |
| SERUM POOLS | | | | | | | |
| Low | 1.6793 | 1.6573 | 1.7357 | 1.7460 | 1.8040 | 1.8690 | 2.0920 |
| Medium | 0.908 | 0.929 | 0.9727 | 1.0073 | 1.0120 | 1.1170 | 1.3080 |
| High | 0.5497 | 0.5603 | 0.5967 | 0.6633 | 0.6690 | 0.7510 | 0.9197 |
| BACK SUB BLK | 0.071 | 0.091 | 0.132 | 0.187 | 0.225 | 0.340 | 0.450 |

*n = 2

Figure 2:
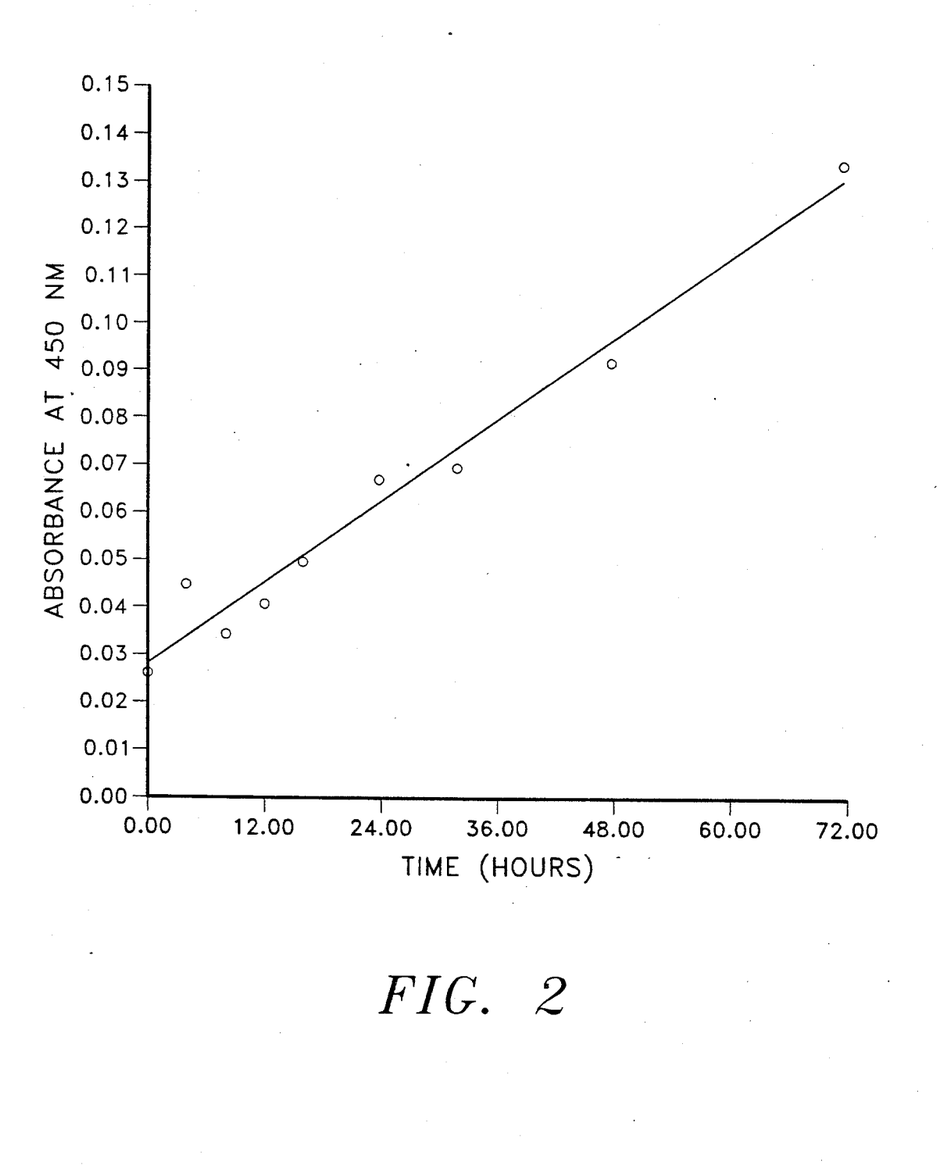
FIG. 2 is a graphic representation of the absorbance increase in substrate blanks in a T4 EIA two-part substrate analysis from 0 to 72 hours.
Figure 3:
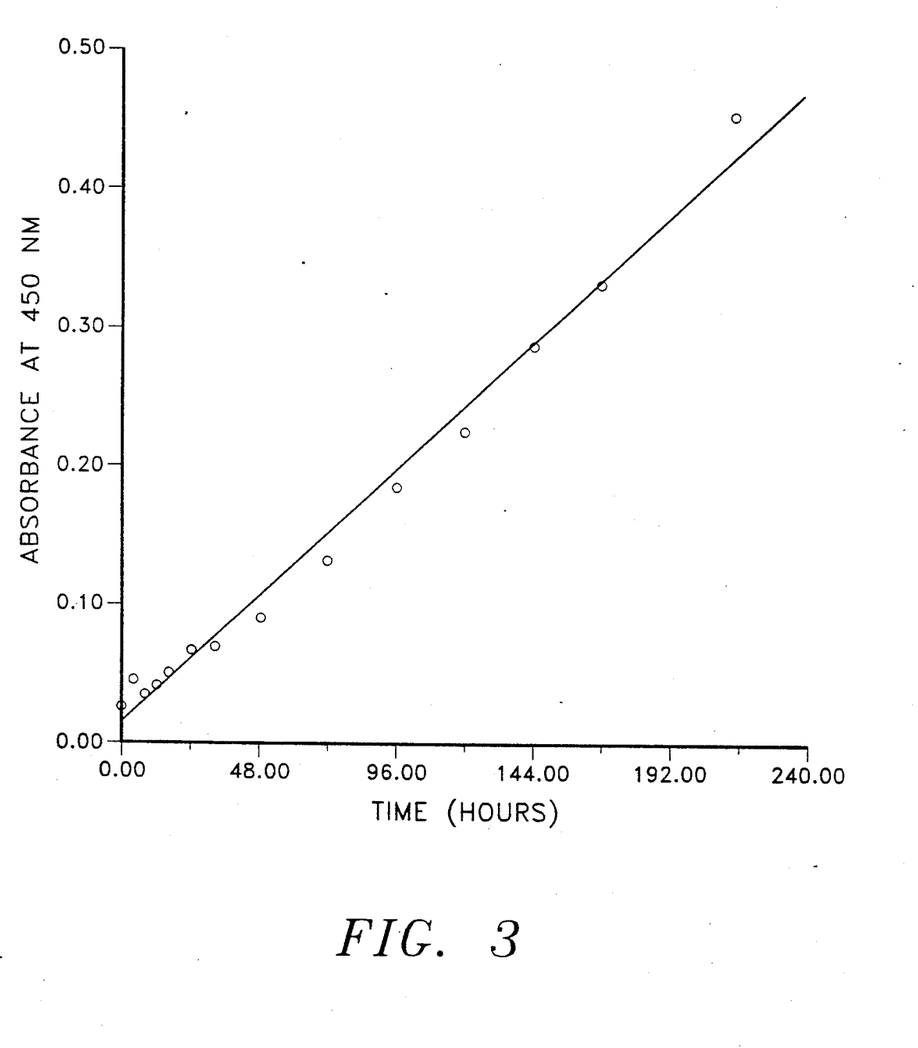
FIG. 3 is an extension of the graphic representation depicted in FIG. 2 over a period of from zero to 216 hours.

The results summarized in Table IV indicate that there was essentially no difference between front and back substrate blanks within each assay, but that between assays, an increase in substrate blank absorbance was obtained. Absorbance increase in substrate blanks is graphically depicted in FIG. 2 (0-72 hours) and FIG. 3 (0-216 hours). The data of Table IV further indicates a general increase in gross absorbance for serum pool and control serum over time.

The gross absorbance data presented in Table IV is further presented in Table V as percent gross absorbance change over time:

TABLE V

Percent Gross Absorbance Change

| SAMPLE | 4 HRS | 8 HRS | 12 HRS | 16 HRS | 24 HRS | 32 HRS |
|---|---|---|---|---|---|---|
| STANDARDS | | | | | | |
| $B_o$ (0 ug/dL) | 9.5 | 5.0 | 5.5 | 9.1 | 9.2 | 4.5 |
| 2.59 ug/dL | 4.3 | 1.3 | 3.8 | 2.8 | 4.2 | −1.5 |
| 4.89 ug/dL | 4.6 | 0.8 | 3.5 | 2.7 | 3.9 | −2.9 |
| 8.95 ug/dL | 5.5 | 2.9 | 4.9 | 6.4 | 8.0 | 2.2 |
| 14.41 ug/dL | 2.5 | 0.3 | 6.1 | 2.5 | 7.4 | 0.4 |
| 24.0 ug/dL | 2.2 | 1.8 | 3.5 | 3.7 | 6.7 | 1.8 |
| CONTROL SERA | | | | | | |
| OMEGA I | 2.6 | 4.0 | 7.2 | 6.4 | 3.5 | 5.5 |
| OMEGA II | 3.8 | 0.9 | 4.6 | 6.1 | 3.3 | 4.1 |
| OMEGA III | 3.4 | 4.9 | 7.4 | 7.4 | 9.0 | 8.4 |
| GILFORD A | 2.5 | 2.3 | 6.4 | 5.8 | 4.9 | 0.8 |
| GILFORD B | 4.8 | 0.8 | 7.0 | 7.3 | 5.3 | 1.8 |
| GILFORD C | 2.3 | −6.6 | 6.3 | 8.4 | 8.2 | 4.7 |
| SERUM POOLS | | | | | | |
| Low | 4.2 | 2.1 | 9.7 | 7.3 | 7.1 | −4.9 |
| Medium | 4.1 | 2.5 | 7.6 | 4.9 | 7.3 | 2.8 |
| High | −0.3 | −3.5 | 4.3 | 4.9 | 6.7 | 4.2 |

| | 48 HRS | 72 HRS | 96 HRS | 120 HRS | 168 HRS | 216 HRS |
|---|---|---|---|---|---|---|
| STANDARDS | | | | | | |
| $B_o$ (0 ug/dL) | 5.1 | 8.7 | 8.8 | 8.8 | 9.1 | 16.4 |
| 2.59 ug/dL | −0.2 | 3.8 | 6.7 | 8.0 | 13.0 | 26.3 |
| 4.89 ug/dL | −0.7 | 2.8 | 7.4 | 8.7 | 14.5 | 35.2 |
| 8.95 ug/dL | 3.6 | 9.4 | 16.5 | 17.8 | 25.5 | 52.6 |
| 14.41 ug/dL | 3.6 | 9.2 | 18.4 | 20.7 | 36.1 | 69.1 |
| 24.0 ug/dL | 6.4 | 15.8 | 26.4 | 34.3 | 54.8 | 101.4 |
| CONTROL SERA | | | | | | |
| OMEGA I | 1.2 | 1.1 | 4.4 | 7.7 | 14.3 | 43.6 |
| OMEGA II | 6.6 | 12.5 | 16.4 | 21.8 | 39.3 | 61.0 |
| OMEGA III | 9.6 | 15.2 | 23.5 | 32.5 | 45.1 | 78.0 |

TABLE V-continued

| | Percent Gross Absorbance Change | | | | | |
|---|---|---|---|---|---|---|
| GILFORD A | −0.6 | 4.1 | 4.8 | 8.2 | 12.1 | 25.5 |
| GILFORD B | 4.2 | 9.1 | 13.0 | 13.5 | 25.3 | 46.7 |
| GILFORD C | 6.7 | 13.7 | 26.3 | 27.4 | 43.1 | 75.2 |
| SERUM POOLS | | | | | | |
| Low | 3.6 | 8.5 | 10.4 | 12.6 | 20.0 | 36.4 |
| Medium | 4.8 | 12.7 | 15.21 | 23.1 | 33.0 | 51.7 |
| High | 1.9 | 11.0 | 19.4 | 23.3 | 36.5 | 61.0 |

To summarize, between 0 and 48 hours after OPD solution preparation, percent increases are relatively low compared to the percent increases at and beyond 72 hours after OPD solution preparation. Percent change is also proportional to the concentration level of the sample. If, however, corresponding run substrate blanks (Table IV) are subtracted from the gross absorbance change values (Table V), i.e., to obtain net absorbance values, the percent changes in net absorbance, as presented in Table VI, are not substantial, particularly during the first 24 hours after preparation of the chromogen solution.

TABLE VI

| | Net Absorbance Percent Change | | | | | |
|---|---|---|---|---|---|---|
| SAMPLE | 4 HRS | 8 HRS | 12 HRS | 16 HRS | 24 HRS | 32 HRS |
| STANDARDS | | | | | | |
| $B_o$ (0 ug/dL) | 8.8 | 4.7 | 4.9 | 8.1 | 7.0 | 2.6 |
| 2.59 ug/dL | 3.0 | 0.7 | 2.8 | 1.2 | 0.6 | −4.6 |
| 4.89 ug/dL | 2.9 | 0.1 | 2.3 | 0.7 | −0.9 | −7.0 |
| 8.95 ug/dL | 3.1 | 1.9 | 3.0 | 3.5 | 1.4 | −3.5 |
| 14.41 ug/dL | −0.9 | −1.2 | 3.6 | −1.8 | −1.8 | −7.7 |
| 24.0 ug/dL | −2.9 | −0.3 | −0.4 | −2.6 | −7.1 | −9.8 |
| CONTROL SERA | | | | | | |
| OMEGA I | 0.90 | 3.42 | 5.76 | 4.18 | −1.47 | 1.37 |
| OMEGA II | 1.27 | 0.0 | 2.65 | 2.80 | −4.57 | −2.31 |
| OMEGA III | 0.20 | 3.93 | 5.03 | 3.31 | −0.47 | 0.47 |
| GILFORD A | 1.46 | 1.90 | 5.44 | 4.38 | 1.86 | −1.84 |
| GILFORD B | 2.89 | 0.12 | 5.33 | 4.71 | −0.35 | −3.10 |
| GILFORD C | −1.02 | −1.22* | 3.93 | 4.24 | −1.43 | −3.61 |
| SERUM POOLS | | | | | | |
| Low | 2.65 | 1.54 | 8.07 | 5.11 | 2.47 | −0.35 |
| Medium | 1.91 | 1.74 | 5.76 | 2.13 | 0.92 | −2.73 |
| High | 0.18 | −4.99 | 2.09 | 1.14 | −2.18 | −3.40 |
| | 48 HRS | 72 HRS | 96 HRS | 120 HRS | 168 HRS | 216 HRS |
| STANDARDS | | | | | | |
| $B_o$ (0 ug/dL) | 2.2 | 4.0 | 1.8 | 0.2 | 0 | −2.7 |
| 2.59 ug/dL | −4.8 | −3.7 | −4.3 | −5.9 | −8.3 | −3.3 |
| 4.89 ug/dL | −6.8 | −7.1 | −7.2 | −9.7 | −13.5 | −3.7 |
| 8.95 ug/dL | −4.9 | −4.3 | −3.8 | −7.9 | −13.9 | −2.0 |
| 14.41 ug/dL | −8.2 | −10.0 | −10.0 | −15.1 | −18.4 | −6.4 |
| 24.0 ug/dL | 11.0 | 12.3 | −15.1 | −17.9 | −24.8 | −8.3 |
| CONTROL SERA | | | | | | |
| OMEGA I | −4.71 | −2.20 | −4.93 | −3.73 | −6.48 | 0.06 |
| OMEGA II | −3.23 | −2.78 | −4.94 | −9.59 | −8.95 | −0.90 |
| OMEGA III | −2.05 | −6.96 | −3.69 | −11.69 | −18.05 | −6.27 |
| GILFORD A | −5.56 | −10.44 | −12.71 | −13.54 | −18.92 | 1.79 |
| GILFORD B | −3.07 | −3.12 | −7.45 | −8.10 | 12.47 | −2.15 |
| GILFORD C | −2.75 | −5.0 | −6.96 | −5.37 | −12.61 | −2.96 |
| SERUM POOLS | | | | | | |
| Low | −2.49 | −1.27 | −4.52 | −6.27 | −9.21 | −3.51 |
| Medium | −3.62 | −0.67 | −5.22 | −2.17 | −6.36 | −2.82 |
| High | −10.73 | −8.10 | −8.82 | −12.78 | −20.31 | −15.32 |

*n = 2

Two-part substrate net absorbance inter-assay precision results from 0 to 24 hours, including standard deviations and the percent coefficient of variation ("percent C.V." or "% C.V."), are presented in Table VII:

TABLE VII

Two-Part Substrate Net Absorbance Inter-Assay Precision For $T_4$ Serum Pools And Control Sera 0 To 24 Hours

| SAMPLE | MEAN ABSORBANCE | S.D. | PERCENT C.V. |
|---|---|---|---|
| CONTROL SERA | | | |
| OMEGA I | 1.009 | 0.0304 | 3.0 |
| OMEGA II | 0.652 | 0.0209 | 3.2 |
| OMEGA III | 0.507 | 0.0143 | 2.8 |
| GILFORD A | 1.682 | 0.0400 | 2.4 |
| GILFORD B | 0.883 | 0.0235 | 2.7 |
| GILFORD C | 0.502 | 0.0154 | 3.1 |
| SERUM POOLS | | | |
| Low | 1.0764 | 0.0319 | 3.0 |
| Medium | 0.768 | 0.0234 | 3.0 |
| High | 0.544 | 0.0186 | 3.4 |

As indicated, the percent C.V. for all samples (n=18) is less than or equal to 3.4 percent.

Table VIII summarizes two-part substrate $T_4$ concentration inter-assay precision from 0 to 24 hours:

TALBE VIII

Two-Part Substrate
$T_4$ Concentration Inter-Assay Precision
0 TO 24 Hours

| SAMPLE | MEAN CONC. ug/dL | S.D. | PERCENT C.V. |
|---|---|---|---|
| CONTROL SERA | | | |
| OMEGA I | 5.6 | 0.258 | 4.6 |
| OMEGA II | 11.1 | 0.412 | 3.7 |
| OMEGA III | 15.6 | 0.462 | 3.0 |
| GILFORD A | 1.6 | 0.137 | 8.5 |
| GILFORD B | 7.0 | 0.231 | 3.3 |
| GILFORD C | 15.9 | 0.551 | 3.5 |
| SERUM POOLS | | | |
| Low | 5.0 | 0.219 | 4.4 |
| Medium | 8.8 | 0.352 | 4.0 |
| High | 14.4 | 0.683 | 4.7 |

Table IX presents $T_4$ sample concentration between 0 and 24 hours, including the percent change from 0 hour to 24 hours:

TABLE IX

| | 0 HOURS | | 24 HOURS | | |
|---|---|---|---|---|---|
| SAMPLE | $T_4$ CONC., ug/dL | % C.V. | $T_4$ CONC., ug/dL | % C.V. | % CHG BETWEEN 0 AND 24 HOURS |
| CONTROL SERA | | | | | |
| OMEGA 1 | 5.71 | 4.94 | 5.79 | 2.11 | 1.4 |
| OMEGA 2 | 11.17 | 3.84 | 11.54 | 4.48 | 3.3 |
| OMEGA 3 | 16.05 | 3.09 | 16.65 | 2.94 | −2.5 |
| GILFORD A | 1.59 | 5.85 | 1.65 | 4.39 | 3.8 |
| GILFORD B | 7.19 | 2.95 | 7.09 | 2.02 | −1.3 |
| GILFORD C | 16.07 | 2.64 | 15.85 | 2.19 | −1.4 |
| SERUM POOLS | | | | | |
| Low | 5.17 | 1.40 | 4.91 | 0.53 | −5.0 |
| Medium | 8.98 | 6.75 | 8.63 | 2.39 | −3.9 |
| High | 14.17 | 6.37 | 14.10 | 0.95 | −0.5 |

No greater than 5.0 percent difference in concentration was evidenced between the 0 and 24 hour measurements.

Percent $B/B_0$ standard curve valves between 0 and 24 hours are presented in Table X.

TABLE X

| STANDARDS ug/dL | 0 HOURS % B/BO | % C.V. | 24 HOURS % B/BO | % C.V. | % CHG OF B/BO FROM 0 TO 24 HRS |
|---|---|---|---|---|---|
| ORIGINAL RUN | | | | | |
| 0 | 100 | | 100 | | |
| 2.59 | 63.98 | 0.6 | 60.01 | 1.1 | −6.2 |
| 4.89 | 48.32 | 0.3 | 44.58 | 0.6 | −7.7 |
| 8.95 | 33.91 | 4.2 | 31.94 | 1.1 | −5.8 |
| 14.41 | 24.13 | 0.1 | 21.89 | 0.9 | −9.3 |
| 24.0 | 16.09 | 1.5 | 13.67 | 1.2 | −15.0 |

The foregoing demonstrates that surprisingly superior increased stability, essential for instrument oriented enzyme immunoassays, is achieved with the disclosed two-part chromogen substrate, over the conventional one-part substrate.

While the foregoing Examples utilized the aforementioned analytical instrument for assay protocol, it should be readily understood that the following claims are not to be limited to applicability only to an instrument or such an instrument. It should, therefore, be understood that the above description is of preferred exemplary embodiments of the present invention, and that the invention is not limited to the specific forms or application shown. Accordingly, the two-part substrate disclosed herein is applicable to other enzyme immunoassay protocols involving enzyme labels.

What is claimed is:

1. A reagent mixture useful in the colorimetric determination of an analyte in an enzyme immunoassay, comprising a mixture of:
    (a) a first solution having a pH between about 4.0 and about 5.5 consisting essentially of an enzyme substrate and a first buffer; and
    (b) a second solution having a pH between about 4.0 and about 5.5 consisting essentially of a second buffer and a chromogenic material selected from the group consisting of o-tolidine, 2-2′-azinobis(3-ethylbenzothiazoline-6-sulfonic acid) diammonium salt, m-phenylenediamine, o-phenylenediamine, dianisidine, aniline, phenol red, pyrogallol, 4-amino antipyrine, and bromopyrogallol red
    wherein the first solution and the second solution are each stable for at least about 24 hours prior to mixture.

2. The reagent of claim 1, wherein said first buffer and said second buffer are substantially the same.

3. The reagent of claim 2 wherein said buffer is selected from the group consisting of phosphate citrate, potassium citrate, and sodium citrate.

4. The reagent of claim 2 wherein said buffer is sodium citrate.

5. The reagent of claim 2 wherein said buffer is phosphate citrate.

6. The reagent of claim 2 wherein the pH of said buffer is about 4.8.

7. The reagent of claim 1 wherein said substrate is a peroxide.

8. The reagent of claim 7 wherein said peroxide is selected from the group consisting of urea peroxide, hydrogen peroxide, methyl peroxide, and ethyl peroxide.

9. The reagent of claim 7 wherein said peroxide is urea peroxide.

10. The reagent of claim 1 wherein said chromogenic material is o-phenylenediamine.

11. The reagent of claim 1 wherein, said immunoassay is a competitive binding immunoassay, said reagent further comprising:
  c) at least one insolubilized binding partner to a ligand of interest; and
  d) a predetermined amount of an enzyme-ligand conjugate.

12. The reagent of claim 11 wherein said enzyme is selected from the group consisting of horseradish peroxidase, catalase, tyrosine oxidase, glucose oxidase, β-D-galactosidase, and alkaline phosphotase.

13. The reagent of claim 11 wherein said enzyme is horseradish peroxidase.

14. The reagent of claim 1 wherein said first solution (a) is mixed with said second solution (b) within at least about 48 hours of said colorimetric determination.

15. The reagent of claim 1 wherein said immunoassay is a non-competitive immunoassay, said reagent further comprising:
  (c) at least one first binding partner to a ligand of interest insolubilized on a solid support; and
  (d) at least one enzyme-labelled second binding partner to said ligand.

16. The reagent of claim 14 wherein said enzyme is selected from the group consisting of horseradish peroxidase, catalase, tyrosine oxidase, glucose oxidase, β-D-galactosidase, and alkaline phosphotase.

17. The reagent of claim 14 wherein said enzyme is horseradish peroxidase.

18. A reagent mixture useful in the colorimetric determination of an analyte in an enzyme immunoassay comprising a mixture of:
  (a) a first solution having a pH between about 4.0 and about 5.0, said solution consisting essentially of a peroxide and a first buffer;
  (b) a second solution having a pH between about 4.0 and about 5.5, said solution consisting essentially of a second buffer and o-phenylenediamine
  wherein the first solution and the second solution are each stable for at least about 24 hours prior to mixture.

19. The reagent of claim 18 wherein the buffer of the first solution and the buffer of the second solution are each independently selected from the group consisting of sodium citrate, phosphate citrate and sodium citrate.

20. The reagent of claim 18 wherein said peroxide is selected from the group consisting of urea peroxide, hydrogen peroxide, methyl peroxide, and ethyl peroxide.

21. The reagent of claim 18 wherein said peroxide is urea peroxide.

22. A reagent mixture useful in the colorimetric determination of an analyte in an enzyme immunoassay, comprising a mixture of:
  (a) a first solution consisting essentially of urea peroxide and sodium citrate buffer, the pH of said solution being within the range of from about 4.0 to about 5.5; and
  (b) a second solution consisting essentially of o-phenylendiamine and sodium citrate buffer, the pH of said solution being within the range of from about 4.0 to about 5.5
  wherein the first solution and the second solution are each stable for at least about 24 hours prior to mixture.

* * * * *

UNITED STATES PATENT AND TRADEMARK OFFICE
CERTIFICATE OF CORRECTION

PATENT NO. : 5,215,885
DATED : June 1, 1993
INVENTOR(S) : David J. Marrujo, et al.

It is certified that error appears in the above-identified patent and that said Letters Patent is hereby corrected as shown below:

Col. 6, line 67, reads "...216 utilizing..." should read --216 hours, utilizing--.

Col. 6, line 68 reads "...addition A and B..." should read --addition reagents A and B--.

Signed and Sealed this

Seventh Day of June, 1994

Attest:

BRUCE LEHMAN

Attesting Officer         Commissioner of Patents and Trademarks